(12) United States Patent
Park et al.

(10) Patent No.: US 9,323,889 B2
(45) Date of Patent: Apr. 26, 2016

(54) SYSTEM AND METHOD FOR PROCESSING REFERENCE SEQUENCE FOR ANALYZING GENOME SEQUENCE

(71) Applicant: SAMSUNG SDS CO., LTD., Seoul (KR)

(72) Inventors: Minseo Park, Seoul (KR); Pan-Gyu Kim, Seoul (KR); Hosang Jeon, Seongnam-si (KR)

(73) Assignee: SAMSUNG SDS CO., LTD., Seoul (KR)

( * ) Notice: Subject to any disclaimer, the term of this patent is extended or adjusted under 35 U.S.C. 154(b) by 702 days.

(21) Appl. No.: 13/713,927

(22) Filed: Dec. 13, 2012

(65) Prior Publication Data
US 2013/0226467 A1    Aug. 29, 2013

(30) Foreign Application Priority Data

Feb. 24, 2012  (KR) .................. 10-2012-0019090

(51) Int. Cl.
*G06F 19/22*     (2011.01)
*G06F 15/00*     (2006.01)
*G06F 19/28*     (2011.01)

(52) U.S. Cl.
CPC .............. *G06F 19/28* (2013.01); *G06F 19/22* (2013.01)

(58) Field of Classification Search
None
See application file for complete search history.

(56) References Cited
PUBLICATIONS

Flicek et al. Sense from sequence reads: methods for alignment and assembly Nature Methods vol. 6, pp. S6-S12 (2009).*
Communication, dated Aug. 22, 2013, issued by the Korean Intellectual Property Office in counterpart Korean Patent Application No. 10-2012-0019090.
Park, Minseo, et al., "Survey of Short Reads Alignment for Next-Generation Sequencing," Samsung SDS Co., Ltd., Oct. 2011, pp. 503-511.
Schmeider, et al.; "Fast Identification and Removal of Sequence Contamination from Genomic and Metagenomic Datasets", PLoS One, Mar. 2011, vol. 6, Issue 3, pp. 1-11.
Camacho, et al.; "BLAST+: Architecture and Applications", BMC Bioinformatics, Dec. 2009, vol. 10, No. 421, pp. 1-9.
LANGMEAD, "Aligning Short Sequencing Reads with Bowtie", Current Protocols in Bioinformatics, Dec. 2010, pp. 1-24.
Communication dated Apr. 17, 2014, issued by the European Patent Office in counterpart European Application No. 12187722.9.
Communication dated Jan. 24, 2014 issued by the Japanese Patent Office in counterpart Japanese Application No. 2012-227089.
Wu, et al., "GMAP: a genomic mapping and alignment program for mRNA and EST sequences", Sequence Analysis, vol. 21, No. 9, Feb. 22, 2005, 18 pgs. total.
Ning, et al., "SSAHA: A Fast Search Method for Large DNA Databases", Genome Research, vol. 11, No. 10, 2001, 6 pgs. total.

* cited by examiner

*Primary Examiner* — John S Brusca
(74) *Attorney, Agent, or Firm* — Sughrue Mion, PLLC

(57) ABSTRACT

Provided are systems and methods for processing a reference sequence. Exemplary systems for processing a reference sequence may include a seed extractor configured to extract a seed from a reference sequence; a determiner configured to determine whether an unidentified base is present or absent in a seed extracted by the seed extractor; and an index generator configured to add a seed to an index when unidentified bases are absent from an extracted seed.

13 Claims, 6 Drawing Sheets

```
REFERENCE SEQUENCE:  G T G G C A A T T A A A T C G T T G G   ...

┌ G T G G C A A T T A
                      │ T G G C A A T T A A
                      │ G G C A A T T A A A
                      │ G C A A T T A A A T
                      │ C A A T T A A A T C
             SEED  ─┤  A A T T A A A T C G
                      │ A T T A A A T C G T
                      │ T T A A A T C G T T
                      │ T A A A T C G T T G
                      └ A A A T C G T T G G

REFERENCE SEQUENCE: G T G G C A A T T A A A T C G T T G G   ...

SEED
- G T G G C A A T T A
- T G G C A A T T A A
- G G C A A T T A A A
- G C A A T T A A A T
- C A A T T A A A T C
- A A T T A A A T C G
- A T T A A A T C G T
- T T A A A T C G T T
- T A A A T C G T T G
- A A A T C G T T G G

REFERENCE
SEQUENCE : ...A C C G T A A A T G N N N N G C C A G C T...

READ :            A T G C T C C G C C

SEED      ↘ ABLE TO MAP THOUGH
                              UNCERTAIN BASE IS PRESENT

US 9,323,889 B2

SYSTEM AND METHOD FOR PROCESSING REFERENCE SEQUENCE FOR ANALYZING GENOME SEQUENCE

CROSS-REFERENCE TO RELATED APPLICATION

This application claims priority from Korean Patent Application No. 10-2012-0019090, filed on Feb. 24, 2012 in the Korea Intellectual Property Office, the disclosure of which is incorporated herein by reference in its entirety.

BACKGROUND

The advent of next generation sequencing (NGS), and the reduction in cost of DNA sequencing, make possible large-scale human genome sequencing for research in medical genetics and population genetics. NGS sequencers used for analyzing reference sequences can produce several billions of very short fragment sequences (referred to as "reads"). The genome sequence of an individual is obtained through resequencing (including indexing, mapping and alignment), and by determining the locations of the generated reads in a reference sequence.

To accurately map reads when analyzing a base sequence, a reference sequence is often used. However, for various reasons (e.g., a sequencing error, a sampling error, a test error, etc.), a reference sequence may contain one or more bases that are of uncertain identity. For example, it is uncertain whether these bases are A, C, G or T. Such unidentified bases are generally denoted as a separate letter, such as "N." To process the unidentified bases, conventional systems for analyzing a base sequence are known that consider the unidentified base as being selected from A, C, G and T, or which predict the identity of the unidentified base using, for example, probabilistic methodology. However, in these conventional systems for analyzing a base sequence, the speed at which a base sequence can be analyzed is considerably reduced, and/or the degree of accuracy in the analysis of a base sequence is reduced, due to the additional processing required for the unidentified base(s).

SUMMARY

One or more exemplary embodiments provide technology for treating an uncertain base in a reference sequence capable of being treated at a high speed without lowering accuracy in analysis of a base sequence.

According to an aspect of an exemplary embodiment, there is provided a system for processing a reference sequence, the system including: a seed extractor configured to extract a seed from a reference sequence; a determiner configured to determine whether an unidentified base is present or absent in the seed extracted by the seed extractor; and an index generator configured to add the seed to an index when unidentified bases are absent from the seed.

According to an aspect of another exemplary embodiment, there is provided a method of processing a reference sequence, the method including: extracting a seed from a reference sequence; determining whether an unidentified base is present or absent in the extracted seed; and adding the seed to an index when unidentified bases are absent from the seed.

According to an aspect of another exemplary embodiment, there is provided an apparatus, including: at least one processor, a memory, and at least one program. The at least one program may be stored in the memory and executed by the at least one processor, and the at least one program may include commands for extracting a seed from a reference sequence, determining whether an unidentified base is present or absent in the extracted seed, and adding the seed to an index when unidentified bases are absent from the seed.

BRIEF DESCRIPTION OF THE DRAWINGS

The above and other objects, features and advantages will become more apparent to those of ordinary skill in the art by describing in detail exemplary embodiments with reference to the attached drawings, in which:

FIG. 1 is a diagram illustrating an example of extraction of a plurality of seeds (depicted, from top to bottom, by SEQ ID NOs: 3-12) from a reference sequence (SEQ ID NO: 1);

FIG. 5 is a diagram illustrating an exemplary process for determining the identity of an unidentified base, through comparison of a reference sequence (SEQ ID NO: 2) with a read (SEQ ID NO: 13)

DETAILED DESCRIPTION OF EXEMPLARY EMBODIMENTS

Figure 2:
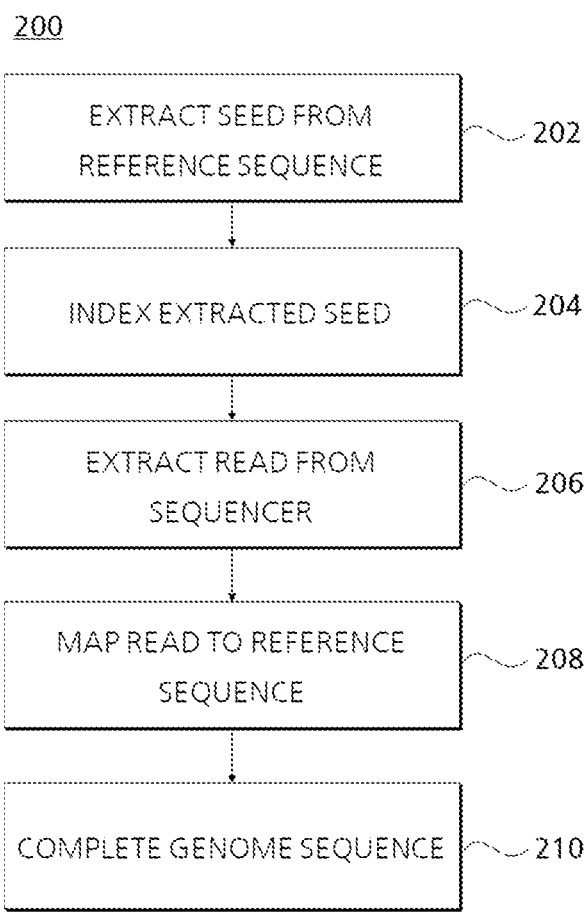
FIG. 2 is a flowchart illustrating an example of genome sequencing.

Hereinafter, exemplary embodiments will be described in detail. However, one or more exemplary embodiments are not limited to exemplary embodiments disclosed below, but can be implemented in various forms. The following exemplary embodiments are described in order to enable those of ordinary skill in the art to embody and practice exemplary embodiments.

Although the terms first, second, etc. may be used to describe various elements, these elements are not limited in their order of appearance or operation by these terms. These terms are only used as expedients to connote the existence of different elements. For example, a first element could be termed a second element, and, similarly, a second element could be termed a first element. The term "and/or" includes any and all combinations of one or more of the associated listed items.

When an element is "connected" or "coupled" to another element, it may be directly connected or coupled to the other element, or one or more intervening elements may be present. In contrast, when an element is referred to as being "directly connected" or "directly coupled" to another element, there are no intervening elements present.

The terminology used herein is for the purpose of describing particular exemplary embodiments only and is not intended to be limiting of exemplary embodiments. The terms "a," "an" and "the" encompass both singular and plural forms, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments will be described in detail below. To aid understanding, like numbers refer to like elements throughout the description of the figures, and the description of the same elements will not be reiterated.

The term "read" is a fragment of a reference sequence that is sequenced and outputted from a genome sequencer. The length of a particular read may vary, and in some embodiments, may be about 35 to 500 base pairs (bp) in length. As those skilled in the art would appreciate, the length of read varies depending on the type of genome sequencing technology employed. DNA bases are generally denoted using the letters A, C, G and T.

The term "reference sequence" refers to a base sequence used to assemble a complete base sequence from the reads. A complete base sequence may be assembled by mapping a large number of reads outputted from a genome sequencer onto a reference sequence.

Reference sequences and reads constitute sequences of bases, with bases in DNA being commonly designated as A, C, G or T, depending on the chemical structure of the base. However, for various reasons (e.g., a sequencing error, a sampling error, etc.), a reference sequence may contain one or more bases that are of uncertain identity. Such bases are generally denoted as a separate letter, such as "N."

The term "seed" is a unit sequence used for mapping reads onto a reference sequence. Theoretically, when mapping reads onto a reference sequence, all the reads should be sequentially compared with the reference sequence, beginning with the first part thereof, in order to estimate the positions in the reference sequence from which each read is produced. However, one disadvantage of this approach is that it requires excessive time and computing power to map a read. For this reason, in practice, a hash table is constructed by hashing a predetermined length of the reference sequence, beginning with the first part thereof, and advancing one base at a time, and then the read is mapped to a position on the reference sequence. In some embodiments, the fragment of the reference sequence for hashing becomes a seed. However, in other embodiments, a fragment of the read may be a seed. In exemplary embodiments, the seed length may be smaller than the length of the read(s), and the seed length may also be adjusted depending on the length of the reference sequence, and/or the capacity of the constructed hash table.

FIG. 1 illustrates an example of extraction of a seed from a reference sequence. In the example, the seed is extracted by extracting the base sequence of the reference sequence one base at a time in a length of 10 bp from the first part thereof. The extracted seeds have the same length (10 bp in the example shown in FIG. 1), but the sequences of the seeds are different from one another depending on the positions of the bases extracted from the reference sequence. In the example shown in FIG. 1, the first extracted seed contains the 1st to 10th bases of the reference sequence, which is G T G G C A A T T A (SEQ ID NO: 3), and the third extracted seed has the 3rd to 12th bases of the reference sequence, which is G G C A A T T A A A (SEQ ID NO: 5).

FIG. 2 is a flowchart illustrating an exemplary method for genome sequencing (S200). It allows the assembly of a complete genome sequence by mapping a large quantity of short reads outputted from a genome sequencer onto a reference sequence.

First, a seed is extracted from a reference sequence (S202). In the exemplary embodiment shown in FIG. 1, a plurality of seeds are extracted by sequentially extracting sequences of bases of a predetermined length from the reference sequence, beginning with the first part thereof, and advancing one base at a time.

Subsequently, the seeds extracted in S202 are hashed using a hash function, and thereby a hash table is produced (S204). The hash table may be keyed with a value generated from the seed. In some embodiments, the value indicates the location in the reference sequence to which the seed corresponds.

Then, a plurality of reads are extracted from a gene by the genome sequencer (S206), and the extracted reads are mapped onto the reference sequence using the hash table (S208).

Figure 3:
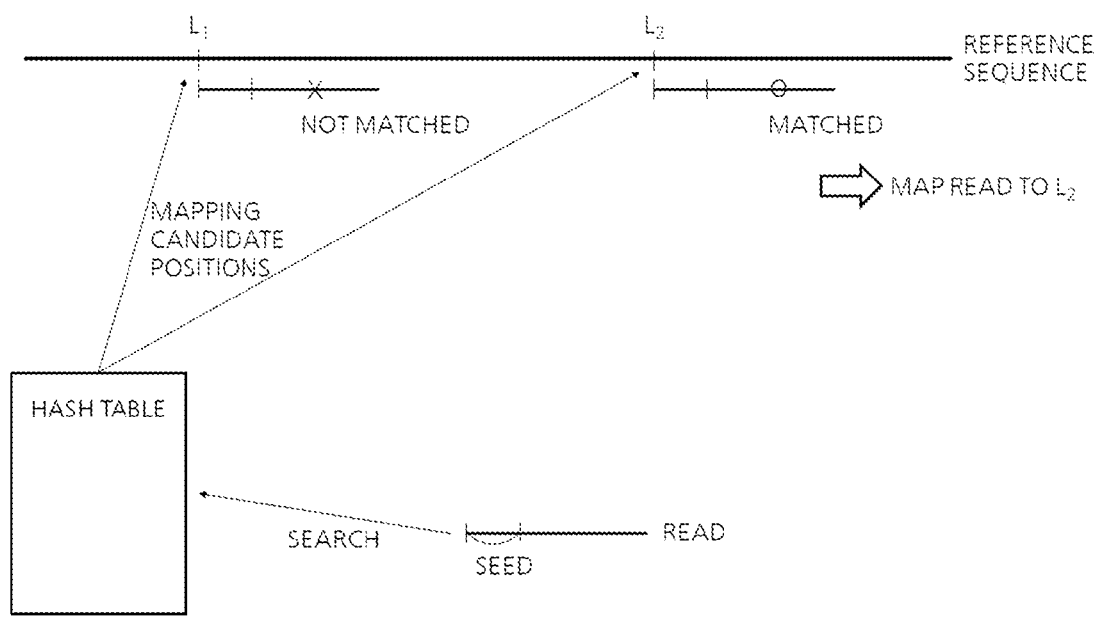
FIG. 3 is a diagram illustrating an example of mapping reads onto a reference sequence during genome sequencing.

FIG. 3 is a diagram illustrating an example of the mapping of reads onto a reference sequence, in the manner described above. First, the N by (N is a seed length) of the read extracted in S206 is read out as a seed, and one or more mapping candidate positions of the seed in the reference sequence are obtained by searching the hash table. In this example, the first part of the read is used as a seed, but in practice, the seed may be any part of the read. However, because the accuracy of the first part of the read is generally high, in some embodiments, the first part of the read is used as a seed. In this case, at least one mapping candidate position is generally obtained (In Table 3, two mapping candidates L1 and L2 are obtained). The number of mapping candidate positions vary depending on seed length.

Subsequently, the remaining part of the read is compared with the reference sequence at each of the mapping candidate positions, to determine an exact mapping position of the read. In the illustrated example, at L1, the read does not correspond to the reference sequence, but the read corresponds to the reference sequence at L2. As a result, the read is mapped to the L2 position.

The reads mapped through the above-described exemplary process are then connected to each other, thereby assembling the reference sequence (S210).

Figure 4:
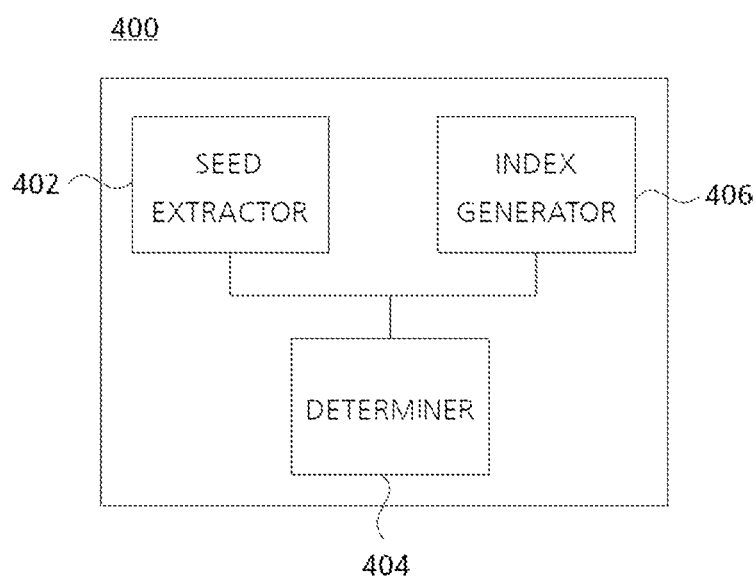
FIG. 4 is a block diagram of an exemplary system for processing a reference sequence.

FIG. 4 is a block diagram of an exemplary system for processing a reference sequence 400. In this exemplary system, the system for processing a reference sequence 400 may be configured as a separate system, or alternatively, may be included as one element in the system for analyzing a reference sequence.

As shown in FIG. 4, an exemplary system for processing a reference sequence 400 includes a seed extractor 402, a determiner 404, and an index generator 406.

The seed extractor 402 extracts a seed from a reference sequence. As described above, the seed extractor 402 extracts a plurality of seeds by sequentially extracting sequences of bases of a predetermined length from the reference sequence, beginning with the first part thereof, and advancing one base at a time. For example, provided that the reference sequence is as follows:

(SEQ ID NO: 2)
A C C G T A A A T G N N N N G C C A G C T

If the predetermined length of a seed is 7 bp, seeds generated from the reference sequence are as follows:

SEED 1:
A C C G T A A

SEED 2:
C C G T A A A

SEED 3:
C G T A A A T

SEED 4:
G T A A A T G

-continued

SEED 5:
T A A A T G N

SEED 6:
A A A T G N N

SEED 7:
A A T G N N N

SEED 8:
A T G N N N N

SEED 9:
T G N N N N G

SEED 10:
G N N N N G C

SEED 11:
N N N N G C C

SEED 12:
N N N G C C A

SEED 13:
N N G C C A G

SEED 14:
N G C C A G C

SEED 15:
G C C A G C T

The determiner 404 determines whether a base that is not identified in a read is identified or not in the seed extracted by the seed extractor 402.

As described above, for various reasons (e.g., a sequencing error, a sampling error, a test error, etc.), a reference sequence may contain one or more bases that are of uncertain identity, and such base(s) are generally denoted as a separate letter, such as "N." Accordingly, the determiner 404 may determine that a base that is not identified in the read is also not identified in the seed, i.e., that the unidentified base is also present in the seed, when a base other than A, C, G or T is present in the seed.

For example, when an unidentified base (e.g., denoted as "N") is present in the reference sequence (and present in a seed extracted therefrom), the determiner 404 may determine whether an unidentified base denoted as "N" is present or absent in the seed. When the unidentified base is present in the seed, it may be determined that an unidentified base present in the read is also not identified in the seed. In addition, when the unidentified base is denoted by a letter other than N, the determiner 404 recognizes such other letter, and determines whether the unidentified base in the read is identified or not in the seed.

In the above-mentioned example, the 11th to 14th bases in the reference sequence are denoted as unidentified (uncertain) bases ("N;" indicated by an underline below), and the 5th to 14th seeds among the seeds extracted from the reference sequence include the unidentified ("N") bases. Accordingly, the determiner 404 determines that an unidentified base in a read is also not identified in the 5th to 14th seeds among the extracted 15 seeds, i.e., the unidentified bases are also present in the 5th to 14th seeds.

(SEQ ID NO: 2)
A C C G T A A A T G N N N N G C C A G C T

The index generator 406 only adds a seed which is determined not to have an unidentified base(s); seeds determined to have an unidentified base(s) are excluded by the determiner 404. Specifically, the index generator 406 hashes a corresponding seed using a hash function when the seed is determined not to have an unidentified base, and generates a hash table using the hashed seed as a key. In the above-mentioned example, the index generator 406 performs indexing only to seeds listed below, excluding the 5th to 14th seeds among the 15 extracted seeds.

SEED 1:
A C C G T A A

SEED 2:
C C G T A A A

SEED 3:
C G T A A A T

SEED 4:
G T A A A T G

SEED 5~14:
excluded from indexing

SEED 15:
G C C A G C T

That is, in an exemplary embodiment, the hash table is generated by extracting seeds from a reference sequence, and excluding those seeds that contain an unidentified base(s). In this way, the analysis speed is dramatically improved without decreasing accuracy, as compared to conventional methods for analyzing base sequences.

Generally, unidentified bases (commonly represented by N) are concentrated in a single location, and make up only about 5% of all the retrieved sequencing data. Accordingly, the exclusion of seeds containing unidentified bases does not decrease significantly the total accuracy of the genome sequencing. In Table 1, the total number of seeds that include an unidentified base ("N") in the reference sequence, according to a seed length k, is calculated.

TABLE 1

| Seed Length (k) | Total Number of Seeds Including N |
|---|---|
| 10 | 222,409,329 |
| 11 | 222,409,622 |
| 12 | 222,409,915 |
| 13 | 222,410,208 |
| 14 | 222,410,501 |
| 15 | 222,410,794 |
| 16 | 222,411,087 |
| 17 | 222,411,380 |

As can be seen from Table 1, when seed length is increased, the total number of seeds including N does not change significantly. As a result, it can be determined that unidentified bases ("N") are mostly concentrated in one location and are continuous in the reference sequence.

In addition, although seeds including an unidentified base are excluded, this generally does not affect assembly of the genome sequence. For example, as shown in FIG. 5, if a seed has a length of 3 bp, the read corresponds to the ATG part of the reference sequence. In this case, the N N N N part of the reference sequence does not correspond to the read, but corresponds to the following G C C part. Therefore, it can be predicted that the uncertain bases are C T C C through comparison with the read. That is, without considering the unidentified ("N") part of the reference sequence, mapping is also possible in an uncertain region through comparison with other parts. Generally, a sequencer extracts reads from one gene through approximately 30 or more repeated operations. Accordingly, when the above-mentioned exemplary method is repeatedly performed using the extracted reads, accurate mapping is also possible with respect to an uncertain part of the reference sequence, and with a very high degree of accuracy.

When a seed length of 15 bp is used, the number of records in the hash table when N is considered as a different letter, such as A, C, G or T, in the reference sequence is as follows:

$5^{15}=30,517,578,125$

In an exemplary embodiment, the number of records in the hash table when N is not considered in the reference sequence is as follows:

$4^{15}=1,073,741,824$

Accordingly, it can be observed that, when N is not considered, compared with the conventional approach when it is, the number of records in the hash table decreases to 1/30.

In addition, when N is considered, 5 letters are used. To express the 5 letters, a minimum of 3 bits are required ($2^2<5<2^3$). Therefore, in this case, the capacity of the hash table is determined as follows:

$(5^{15}=30,517,578,125) * 3$ bits

However, it can be observed that, when N is not considered, the letters can be expressed with two bits ($2^2=4$), and the capacity of the hash table is calculated as follows:

$(4^{15}=1,073,741,824) * 2$ bits

Thus, when the capacity of the hash table is considered, compared with the conventional approach, the hash table capacity decreases to approximately 1/45.

Figure 6:
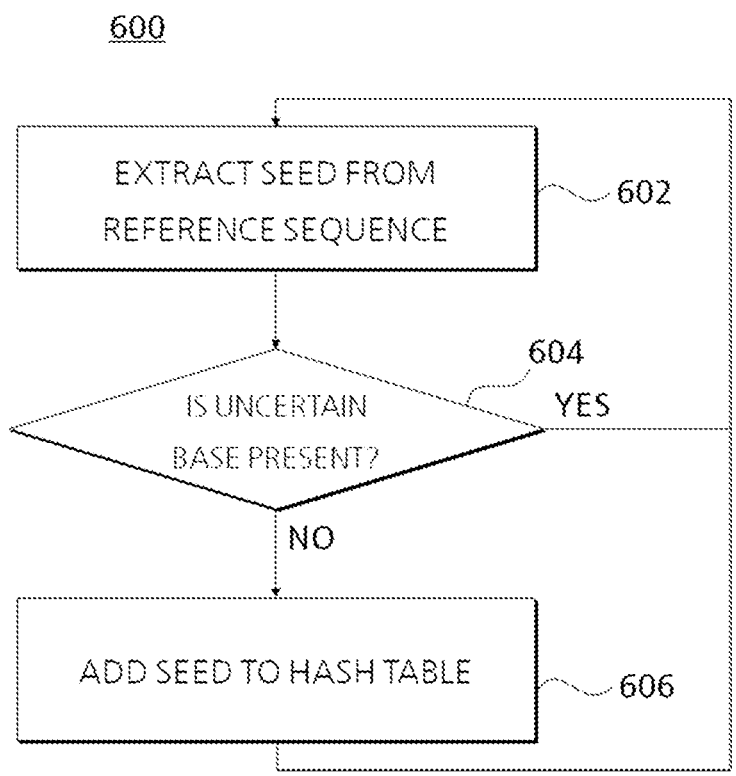
FIG. 6 is a flowchart illustrating an exemplary method for processing a reference sequence.

FIG. 6 is a flowchart illustrating an exemplary method of processing a reference sequence (S600).

First, a seed is extracted from a reference sequence (S602), and it is determined whether an unidentified base in a read is also unidentified in the extracted seed (S604), i.e., whether the unidentified base is also present in the seed. As described above, in S604, when a base denoted by a letter other than A, C, G or T is present in the seed (e.g., when a base represented by N is present), it can be determined that the unidentified base in the read is also unidentified in the seed.

When it is confirmed that the unidentified base in the read is also unidentified in the seed, the seed is excluded from generation of an index. That is, a seed including an unidentified base is not used in subsequent mapping. In contrast, when an unidentified base in a read is not unidentified in the seed, the seed is added to a hash table (S606).

In some embodiments, the processes in S602 to S606 are repeated until analysis of a base sequence is sequentially performed from the first part of the reference sequence to the last part thereof, and a seed index for analyzing a base sequence is generated through the above-mentioned process.

In other embodiments, a computer-readable recording medium is provided which includes a program for performing methods described herein on a computer. The computer-readable recording medium may include a program command, a local data file, and a local data structure, used alone or in combination. The medium may be specially designed or configured for the present invention, or known to those of ordinary skill in the field of computer software. Examples of the computer-readable recoding medium include magnetic media such as a hard disk, a floppy disk and a magnetic tape, optical recording media such as a CD-ROM and a DVD, a magnetic-optical medium such as a floppy disk, and hardware devices specially configured to store and execute program commands such as a ROM, a RAM and a flash memory. The program commands may include a high-level language code capable of being executed by a computer using an interpreter, as well as machine code, which is, for example, made by a compiler.

Thus, in exemplary embodiments, since an algorithm for processing an unidentified base may be omitted from analysis of a reference sequence, whilst still maintaining accuracy, the process of analyzing a base sequence can be simplified, and the analysis time can be drastically reduced.

Further, in exemplary embodiments, the capacity of a hash table is drastically reduced, and thus it is possible to analyze a base sequence with a smaller memory.

While exemplary embodiments have been shown and described above, it will be understood by those skilled in the art that various changes in form and details may be made therein without departing from the scope of the inventive concept as defined by the appended claims.

SEQUENCE LISTING

<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 1
gtggcaatta aatcgttgg                                                19

<210> SEQ ID NO 2
<211> LENGTH: 21
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (11)..(14)
<223> OTHER INFORMATION: n is a, c, g, or t

<400> SEQUENCE: 2

```
accgtaaatg nnnngccagc t                                              21

<210> SEQ ID NO 3
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 3
gtggcaatta                                                           10

<210> SEQ ID NO 4
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 4
tggcaattaa                                                           10

<210> SEQ ID NO 5
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 5
ggcaattaaa                                                           10

<210> SEQ ID NO 6
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 6
gcaattaaat                                                           10

<210> SEQ ID NO 7
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 7
caattaaatc                                                           10

<210> SEQ ID NO 8
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 8
aattaaatcg                                                           10

<210> SEQ ID NO 9
<211> LENGTH: 10
<212> TYPE: DNA
```

```
<213> ORGANISM: Artificial Sequence
<220> FEATURE:
<223> OTHER INFORMATION: Synthetic polynucleotide

<400> SEQUENCE: 9
attaaatcgt                                                              10

<210> SEQ ID NO 10
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 10
ttaaatcgtt                                                              10

<210> SEQ ID NO 11
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 11
taaatcgttg                                                              10

<210> SEQ ID NO 12
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 12
aaatcgttgg                                                              10

<210> SEQ ID NO 13
<211> LENGTH: 10
<212> TYPE: DNA
<213> ORGANISM: Artificial Sequence
<220> FEATURE:
<223> OTHER INFORMATION: Synthetic polynucleotide

<400> SEQUENCE: 13
atgctccgcc                                                              10
```

What is claimed is:

1. An apparatus for processing a reference sequence, comprising:
   at least one hardware processor;
   computer-readable memory, said memory comprising one or more programs, executed by the at least one hardware processor, which comprise commands for:
   extracting a seed from a reference sequence;
   determining whether an unidentified base is present or absent in the extracted seed; and
   adding the seed to an index when unidentified bases are absent from said extracted seed.

2. The apparatus of claim 1, wherein the apparatus determines that an unidentified base is present in a seed when a base denoted by a letter other than A, C, G or T is present in a seed.

3. The apparatus of claim 1, wherein the apparatus determines that an unidentified base is present in a seed when a base denoted by the letter N is present in a seed.

4. The apparatus of any one of claims 1 to 3, wherein said apparatus is for analyzing a genome sequence, and wherein said apparatus is configured to receive reads outputted from a genome sequencer.

5. A method for processing a reference sequence, comprising the steps of:
   (1) extracting a seed from a reference sequence;
   (2) determining whether an unidentified base is present or absent in the extracted seed; and
   (3) adding the seed to an index when unidentified bases are absent from said extracted seed,
   wherein steps (1)-(3) are performed using the apparatus of claim 1.

6. The method of claim 5, wherein an unidentified base is determined to be present in said extracted seed when a base denoted by a letter other than A, C, G or T is present in said extracted seed.

7. The method of claim 5, wherein an unidentified base is determined to be present in said extracted seed when a base denoted by the letter N is present in said extracted seed.

8. The apparatus of claim 1, wherein said one or more programs further comprise: commands for extracting a plurality of seeds from the reference sequence; commands for hashing seeds which do not contain unidentified bases using a hash function; and commands for generating a hash table using the hashed seeds as keys.

9. The apparatus of claim 8, wherein the plurality of seeds are extracted from the reference sequence by sequentially extracting sequences of bases of a predetermined length from the reference sequence.

10. The apparatus of claim 8, wherein said one or more programs further comprise commands for keying the hash table with a value indicating the location in the reference sequence that the seed corresponds to.

11. The method of claim 5, wherein said method comprises extracting a plurality of seeds from the reference sequence, and wherein said method further comprises hashing seeds which do not contain unidentified bases using a hash function, and generating a hash table using the hashed seeds as keys.

12. The method of claim 11, wherein said plurality of seeds are extracted by sequentially extracting sequences of bases of a predetermined length from the reference sequence.

13. The method of claim 11, wherein said method further comprises keying the hash table with a value indicating the location in the reference sequence that the seed corresponds to.

\* \* \* \* \*